United States Patent
Bienert et al.

(10) Patent No.: US 6,506,611 B2
(45) Date of Patent: Jan. 14, 2003

(54) METERING HEAD FOR PARALLEL PROCESSING OF A PLURALITY OF FLUID SAMPLES

(75) Inventors: Klaus Bienert, Potsdam (DE); Andreas Vente, Berlin (DE); Heiko Kraack, Potsdam (DE); Rolf Zettl, Berlin (DE)

(73) Assignee: Deutsches Resourcenzentrum fur Genomforschung GmbH (DE)

( * ) Notice: Subject to any disclaimer, the term of this patent is extended or adjusted under 35 U.S.C. 154(b) by 0 days.

(21) Appl. No.: 09/776,742

(22) Filed: Feb. 5, 2001

(65) Prior Publication Data

US 2001/0019845 A1 Sep. 6, 2001

Related U.S. Application Data (63) Continuation of application No. PCT/EP99/05715, filed on Aug. 6, 1999.

(30) Foreign Application Priority Data

Aug. 7, 1998 (DE) .......................................... 198 35 833

(51) Int. Cl.[7] ................................................. B01L 30/02
(52) U.S. Cl. ................. 436/180; 73/864.17; 73/864.24; 73/864.25; 422/100
(58) Field of Search ......................... 422/100; 436/180; 73/864.17, 864.24, 864.25

(56) References Cited

U.S. PATENT DOCUMENTS

| | | | |
|---|---|---|---|
| 4,598,840 A | * | 7/1986 | Burg |
| 5,055,263 A | | 10/1991 | Meltzer |
| 5,497,670 A | | 3/1996 | Carl |
| 5,645,723 A | | 7/1997 | Fujishiro et al. |
| 5,660,792 A | | 8/1997 | Koike |
| 5,736,105 A | | 4/1998 | Astle |
| 5,770,860 A | | 6/1998 | Franzen |

FOREIGN PATENT DOCUMENTS

| | | |
|---|---|---|
| DE | 282 082 | 8/1990 |
| DE | 196 28 178 | 9/1997 |
| DE | 197 54 000 | 6/1999 |
| EP | 0 289 946 | 11/1988 |
| EP | 0 514 948 | 11/1992 |
| JP | 63-131067 | 6/1988 |
| JP | 0 912 17 33 | 5/1997 |
| WO | WO 86/02168 | 4/1986 |
| WO | WO 99/30168 | 6/1999 |

OTHER PUBLICATIONS

Packard, "MultiPROBE", Automated Multichannel Liquid Handling Systems 5/93.

* cited by examiner

Primary Examiner—Jan Ludlow
(74) Attorney, Agent, or Firm—Schnader Harrison Segal & Lewis LLP (57) ABSTRACT

A freely traversable metering head with numerous metering devices, wherein the metering devices are each provided individually or block-by-block with an activating device, and wherein a controller traversable with the metering head is designed for the independent operation of one or more activating devices. Metering devices for such a metering head and procedures for their use are also disclosed.

19 Claims, 6 Drawing Sheets

METERING HEAD FOR PARALLEL PROCESSING OF A PLURALITY OF FLUID SAMPLES

RELATED APPLICATION

This is a continuation of International Application No. PCT/EP99/05715, with an international filing date of Aug. 6, 1999, which is based on German Patent Application No. 198 35 833.4, filed Aug. 7, 1998.

FIELD OF THE INVENTION

This invention relates to a metering head for holding, moving and releasing fluid samples, in particular a metering head having a plurality of metering devices, which can be manipulated with a picking/spotting system. The invention also relates to a procedure for using such a metering head.

BACKGROUND

In biochemistry, molecular genetics and medicine, there is an interest in manipulating dissolved or suspended substances for purposes of detection, analysis, reaction or synthesis. Often large number of samples with small sample volumes must be processed. To this end, so-called picking/spotting systems were developed, which are used to transfer samples from one location on a carrier substrate (e.g., on a microtiter plate) to another location on this or another carrier substrate.

Generally known from practice are picking/spotting systems that have a robotic head with picking needles arranged in a matrix for sample manipulation. To manipulate samples, the robotic head is guided over a microtiter plate. The pickling needles are individually and sequentially dipped in the desired microtiter volumes, with samples being taken through adhesion of the fluid to the needle tip.

Conventional picking/spotting systems with robotic heads based on picking needles have the following disadvantages. To move the robotic heads with pickling needles in numbers of practical interest, e.g., 96, as rapidly and unobstructedly as possible, efforts have previously been made to keep the number of supply lines from the stationary system to the moved robotic head as low as possible. For example, this is achieved by using matrix circuits, in which a supply line is routed to each row of needles and each column of needles in the matrix array, so that needles can be actuated by activating the rows and columns associated to a specific needle. While this substantially reduces the number of lines, it has resulted in a situation where the robotic heads can only be operated sequentially, i.e., needle for needle in sequence. This is disadvantageous for the entire duration of the operation steps intended for a microtiter plate, for example. This is problematic not just relative to the large numbers of samples to be processed, but also limiting if only a specific reaction time is available for processing.

As an alternative to the mentioned matrix actuation, robotic heads are known in which a plurality of needles share a common activation unit which can be moved over the back side of the matrix array. For example, a metering head is generally known in which an activation unit (e.g., in the form of a pneumatic cylinder) is moved, using an adjusting compound table, to the position of a needle to be actuated. This technique also permits only a sequential needle actuation by passing the sole activation unit sequentially over the respective needles to be actuated. Therefore, this structural design poses the same problems as encountered in the matrix activation configuration described above.

If emphasis is not being placed on the aforementioned efforts to minimize the number of supply lines, it is known that metering heads can be provided with several metering devices having separate supply lines. Such a metering head is described, for example, in U.S. Pat. No. 5,055,263. However, the metering devices in metering heads of this type are generally provided with a stepping-motor drive. This limits how densely the metering devices can be arranged. Stepping-motor driven metering devices cannot be arranged in a matrix corresponding to the grid of conventionally used microtiter plates. This causes problems in the processing of samples from microtiter plates. Another disadvantage to the metering heads with individually actuatable metering devices has to do with the fact that the metering head is an integrated component to make it as light as possible. The metering devices are rigidly connected with an actuating unit, and cannot be adjusted to special applications (adapted to sample volume, sample shape, etc.).

Another problem associated with conventional robotic heads with picking needles is that sample uptake or release cannot be metered. The amount of sample absorbed by adhesive forces while dipping a picking needle into a fluid depends on the substance, and varies with immersion depth. Sample release cannot be reproduced either. In addition, only very small sample quantities can be processed or transferred.

Another disadvantage encountered with conventional spotting robots involves the transfer of samples between substrates with various geometric formats. For example, in cases where PCR products were taken up by a microtiter plate (usually in a 16×24 grid with 384 recesses) and placed on a glass carrier, needle matrixes with a grid of 4×4 needles adapted to the glass carrier (e.g., slide) were previously used. Therefore, only 16 clones could be transferred in a single operation step (uptake of clone and application to glass carrier). The needle matrix with the small grid must subsequently first be washed, sterilized and dried, so that new clones can be transferred. Therefore, a total of 24 transfer steps and wash cycles have previously been necessary for 384 samples. This is associated with a high time outlay and low sample throughput, and with a disadvantages relating to the accuracy of sample placement on the glass carrier. After each sample is deposited, the 4×4 needle matrix is passed over the metering head for a relatively long distance. The long travelling paths give rise to inaccuracies in positioning, so that the sample density on the glass carrier is limited, or the sample array is not reproducible. As a result, ensuing verification procedures (e.g., optical sample measurement, fluorescence measurement) cannot be fully utilized with the local resolution available today.

One general disadvantage to conventional metering heads involves their limitation to pure metering tasks. However, sample manipulation also requires that plate-shaped substrates or microtiter plates with samples be moved between various processing stations. To this end, a separate manipulator head must be used in conventional laboratory systems.

Thus, it would be advantageous to provide for a metering head improved over conventional robotic heads of picking/spotting systems which increases the rate at which a plurality of samples are processed, and has a sufficiently simple structure so as not to limit the ability of the metering head to move or travel compared to conventional robotic heads. In particular, it would be advantageous to have a metering head wherein predetermined sample quantities can be taken up or released with an increased accuracy and reproducibility. Also, providing procedures to use such a metering head would be helpful.

SUMMARY OF THE INVENTION

This invention relates to a metering head that can be freely traversed by an actuating device and having a plurality of metering devices, which, as individual metering devices or as metering device blocks, are provided with respective activating devices individually or in blocks. The metering devices comprise: picking needles or micropipettes arranged in accordance with orientation of sample volumes in a microtiter plate, the activating devices each being formed by a pneumatic cylinder having an actuating needle for activating the metering devices or metering device blocks, and a controller traversable with the metering head provided with control output whose number at least equals the number of pneumatic cylinders and which are connected with an accompanying control output by a pressure line, such that the metering devices or metering device blocks can be independently activated during metering head operation.

BRIEF DESCRIPTION OF THE DRAWINGS

Additional advantages and particulars of the invention will be described below with reference to the attached drawings, in which.

DETAILED DESCRIPTION

According to a first important aspect of the invention, a metering head is provided that can be freely traversed with by actuating device and has a plurality of metering devices separately activatable for sample uptake or release, which can each be actuated with an accompanying activating element (adjusting and switching elements), wherein a controller traversable together with the metering head is provided, with which each activating element can be operated individually and independently of the activation of remaining activating elements. "Metering" implies not just quantitative dosing of substance quantities, but generally refers to any qualitative or quantitative process for sample uptake, release, transfer, movement or the like. Correspondingly, any means for metering specific sample quantities can be used as the metering device. These include all pipetting, dripping, suction, pumping, jet, spray or other dispensing devices for metering predetermined fluid quantities. However, the invention is preferably implemented with metering devices for metering the smallest fluid quantities in the nl or µl range, e.g., with the mentioned picking needles or micropipettes or microdispensers.

The actuators for activating the metering devices are designed to depend on the shapes of the devices. Depending on the application, any mechanical actuating element can be provided, which is electromagnetically, hydraulically or pneumatically activatable. In the microdrop metering devices mentioned, hydraulically or pneumatically actuated actuating cylinders (hereinafter: pneumatic cylinders) are preferably used as the actuating elements. In this case, each pneumatic cylinder is connected with the operating pressure line by a pressure line and a valve activatable by the controller.

The controller is part of the metering head. It comprises a circuit having in particular a command input and numerous control outputs corresponding to the number of actuating elements. Depending on a predetermined control signal at the command input, the controller is set up to activate one or more of the control outputs in a chronologically simultaneous, delayed or separate manner with electrical control signals independently of each other, in response to which the actuating elements are triggered. The controller preferably consists of a microprocessor having a serial interface as the command input and the mentioned plurality of control outputs. The serial interface is connected with the main computer, e.g., a picking/spotting system.

To meter the microdrops, the metering devices are preferably routinely arranged on the metering head in a manner corresponding to the relative array of samples on a substrate carrier. The arrangement is preferably tailored to work operations on microtiter plates. In this case, the metering devices are aligned like a matrix based on the matrix configuration of the microtiter volumes. Correspondingly, the actuating elements also are arranged in a matrix, referred to in the following as the actuating matrix or pneumatic cylinder matrix. An important feature of the invention is that the metering devices or actuating matrix are freely addressable, providing for the first time a metering head wherein the metering devices operate in parallel.

A modular system can also be provided, in which the actuating matrix is permanently integrated on the metering head to form a projection for freely selectable, replaceable blocks with various types of metering devices.

According to a second important aspect of the invention, a metering head is provided with a plurality of pickling needles or micropipettes, which are arranged in a matrix on a mounting block that interacts with a freely addressable actuating matrix. The micropipettes are uniformly secured to the mounting block in such a way that, in the basic position, the ends of activating pins (pipette pistons) of the micropipettes essentially lie in one plane, and contact the ends of actuating needles or pins of the actuating matrix. The activating pin of a micropipette is biased by means of a pin spring against the micropipette. When an actuating element of the actuating matrix (e.g., of a pneumatic cylinder) is operated, the corresponding activating pin is pressed against the pin spring, thus reducing the pipette volume. When the actuating element is released, the spring-loaded pin presses back the activating pin, so that the pipette volume increases again. The same applies when using picking needles.

For the first time, this arrangement provides for a metering head permitting reproducible and precise metering of a plurality of simultaneously processed samples.

According to a third important aspect of the invention, the metering head with the micropipette matrix is provided with a guide on the mounting block, so that, when the respective actuating element is operated, the corresponding micropipette is first moved from a retracted basic position to a projecting pipetting position relative to the mounting block before the pipetting volume changes. For the first time, a metering head is provided thereby in which, as with the projecting picking needles, micropipettes are selectively moved into the pipetting position and activated individually or simultaneously in a freely addressable manner. During interaction with a microtiter plate, for example, this prevents immersion, and hence contamination, of micropipettes not in use during the respective process.

Therefore, the invention also relates to the combination of a micropipette that exhibits a cylinder, a pipette tip and a pipette piston, which is biased relative to the cylinder by means of a pin spring, with a carrier or mount that allows the micropipette to be moved relative to the carrier parallel to the longitudinal direction of the pipette. The cylinder of the micropipette is biased relative to the carrier with a cylinder spring. The micropipette is moved relative to the carrier between two end positions via the maximal expansion or maximal compression of the cylinder spring. According to the invention, the spring rate of the cylinder spring is significantly lower than that of the pin spring, so that the pipette can be made to move by an axial force on the pipette piston.

The double-spring guide for the micropipette or pipette piston makes it possible, by simply activating the pipette piston, to initially advance the micropipette into a pipetting position relative to the carrier, and then activate the pipette piston.

According to a fourth important aspect of the invention, a metering head with a plurality of metering devices is provided, which are connected, rather them individually, but in groups or blocks to an activating device. In this case, the controller provided on the metering head, and adopted to be traversed therewith, has a number of control outputs corresponding to the number of formed groups or blocks of metering devices, wherein one or more blocks can be activated independently from each other during metering head operation. This embodiment of the invention is provided in particular for transferring samples from one arrangement with a first geometric format into a target arrangement with a second, different format. The first format is given by the matrix arrangement of a microtiter plate, for example. The second format can be in the form of a target that has been altered relative to the microtiter plate, e.g. a glass target shaped as a slide. In the invention, metering devices (e.g., needles or micropipettes) are combined with coupling units or block frames into blocks, so that the arrangement of metering devices formed by one block has a format that corresponds to the format of a predetermined target. One preferred block formation comprises 4×4 metering devices, which each are combined into a single block. Block formation offers special advantages for sample metering between sample arrays of varying formats and, in particular, when providing sample arrays on glass carriers with a sample density adapted to the improved resolutions in modern optical detection procedures.

Additional important aspects of the invention involve the attachment of a lid station and gripper station on the metering head. This integrated structure permits a more effective handling of carrier substrates and their covers.

During application of the invention, the aspects raised above can be realized together or separately.

The invention offers the following advantages. Sample processing is greatly accelerated, in particular, with respect to molecular genetic, biochemical or medical applications. The samples remain in the metering head for shorter periods of time, and hence are treated gently. The new metering head is universally applicable. The accuracy of metering is increased. Since the substrate carrier covers are not left open as long, the danger of contamination and evaporation is reduced. In the metering head according to the invention, the metering devices are not securely connected with the actuating unit, but rather the modules are interchangeable. As a result, the field of application of the metering head is expanded considerably. This also stems from the combination of metering function with the functions of manipulating substrates or microtiter plates. A separate control computer can be included in the metering head, according to the invention. Hence, the metering head is freely programmable, and can be adapted particularly well even to complicated sample manipulation tasks.

Figure 1A:
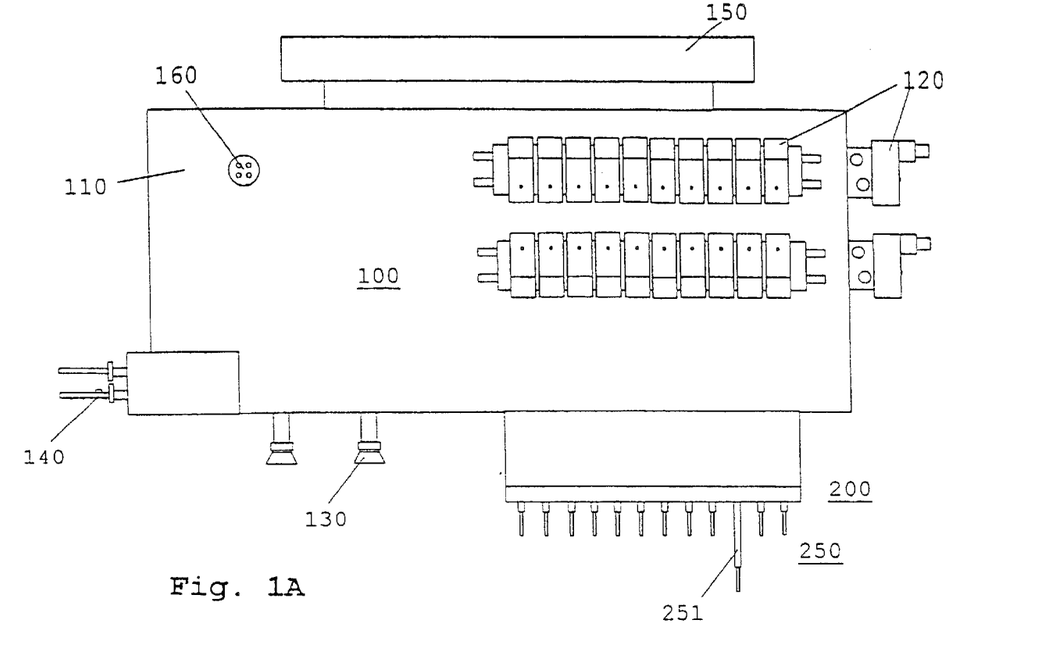
FIG. 1A is a diagrammatic side view of a metering head according to the invention.

Turning now to the drawings, FIG. 1A shows a diagrammatic side view of a metering head 100 according to the invention. Secured to the frame or casing 110 are a metering station 200 (see FIG. 2) with a plurality of metering devices 250, a plurality of switching elements 120, which are each associated with an actuating element (not shown) for each metering device, a lid station 130, a gripper station 140, a mount 150 set up for connection with a traversing drive, e.g., a picking/spotting system, and terminal connections 160 for the supply lines. Each of the switching elements 120 has a separate control connection with the controller (not visible) in casing 110. The control connection of a switching element is linked exclusively with one control output of the controller, and separated from the remaining switching elements.

In the embodiment shown, the metering devices 250 of the metering station 200 are picking needles or pins 251. The metering station 200 is attached to the lower side of the metering head 100 in the operating position. The picking needles are regularly aligned and project from a carrier plate in such a way that the needle ends lie essentially in a single plane in a retracted basic position. Depending on how the actuating elements associated to the needles are operated (see below), one or more picking needles (e.g., pin 251) can be traversed from the basic position into a projecting sample position. The freely and independently actuatable picking needles advantageously result in extended potential uses and applications when compared to the function of a conventional picking/spotting robotic head. This concerns in particular to sample resorting, which is of interest when resorting clone libraries ("rearraying"), for example. In this case, a small quantity of viable organisms are taken from mother plates (microtiter plates) using needles, and transferred to sister plates filled with a fluid medium. The advantage compared to the previous sequential rearraying is the parallel processing of numerous clone transfers. This not only distinctly reduces the overall time expended, but also decreases the influence of disadvantageous environmental conditions.

The switching elements 120 are electrically operable solenoid valves that exert an operating pressure (e.g., ranging from about 5–about 10 bar) provided by an operating pressure supply line (not shown) on the respective actuating element in the form of a pneumatic cylinder in response to a switching or control signal from the controller. A pressure line (not shown) inside the casing 110 leads from each solenoid valve to the respective pneumatic cylinder.

The lid station 130 is provided for the occasional opening of sample or reaction containers or covers of microtiter plates. The sample or reaction containers or microtiter plates can also be transported with the gripper station 140 (parallel gripper) of the metering head. The integrated attachment of the lid station 130 and gripper station 140 to the metering head 100 has the additional advantage of extending even further the multifunctionality of the metering head achieved by the parallel actuation of metering devices.

The depicted metering head 100 is roughly 35 cm wide and 15 cm (casing with mount) or 20 to 25 cm (in area of metering station) high. The accompanying casing depth (with switching elements) measures roughly 30 cm. The number of picking needles is 96 or 384, for example. An important advantage to the invention is that, for the first time, such a large number of metering devices are attached to the metering head together with the respective pneumatic cylinders or actuating elements. By shifting the switching processes from a fixed basic system (e.g., picking/spotting system) in the metering head, the ability of the metering head to freely traverse with practicable travelling speeds is ensured despite the high number of metering devices.

The picking needles 251 of the metering station 200 according to FIG. 1A can be directly attached to the pneumatic cylinders, if these are equipped with suitable retracting springs. According to a preferred design, the picking needles are secured to the carrier plate 240 (see FIG. 2) with springs, as explained in detail below with reference to micropipettes. Attaching the freely activatable matrix of actuating elements (pneumatic cylinders) to the metering head makes it possible to use carrier plates with metering devices of varying type depending on application, which can then be adjusted by the pneumatic cylinders. It is possible to detachably or replaceably secure the carrier plate 240 to the metering station 200 with suitable attachment or latching means (not shown).

Figure 1B:
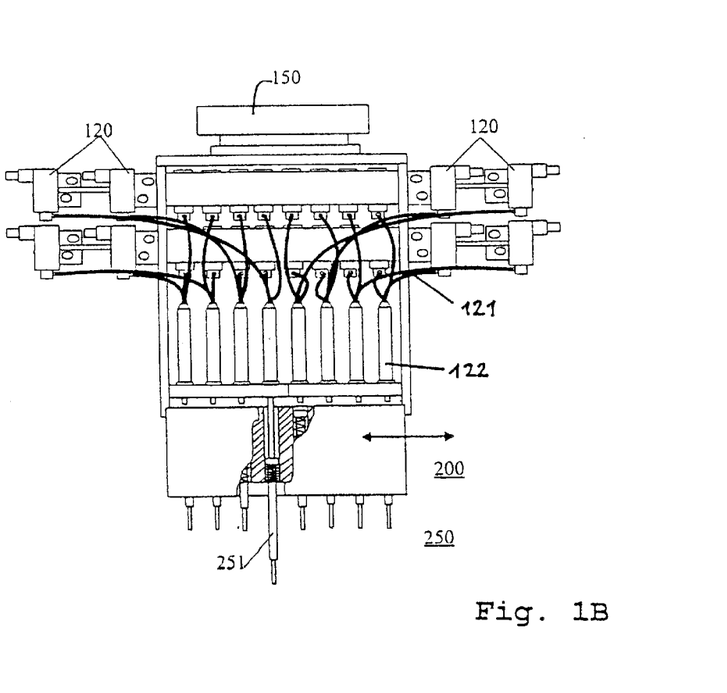
FIGS. 1B–1D are related views of a metering head according to the invention from the sides and bottom, with additional details illustrated.
Figure 1C:
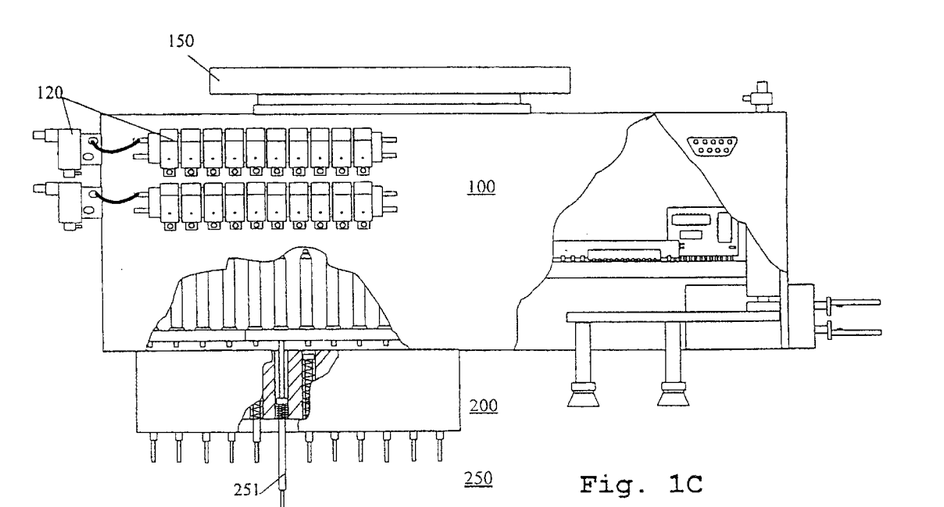
Figure 1D:
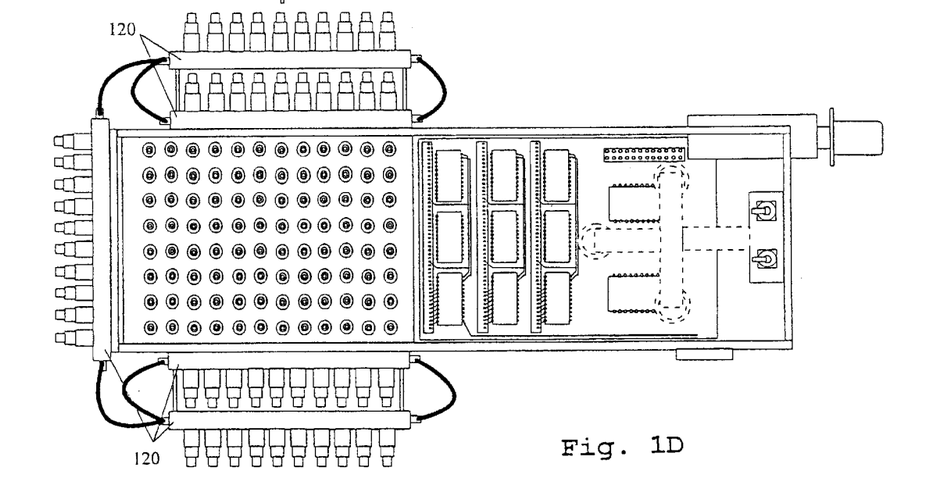

FIG. 1B to 1D illustrate additional details of a metering head 100 according to the invention. The structure of the metering head 100 essentially corresponds to that of metering head 100 according to FIG. 1A, so that the corresponding components are labelled with the same reference signs. Additionally shown relative to FIG. 1A are the pressure lines 121 from the switching elements 120 to the pneumatic cylinders 122. The provision of pneumatic cylinders as a drive for the metering devices represents a significant advantage to the invention. The pneumatic cylinders can be arranged considerably more densely than conventional stepping-motor drives, for example. In addition, FIGS. 1C and 1D illustrate the accommodation of a complete control computer in the metering head according to the invention. Details of the metering station 200 will be described below.

Figure 2:
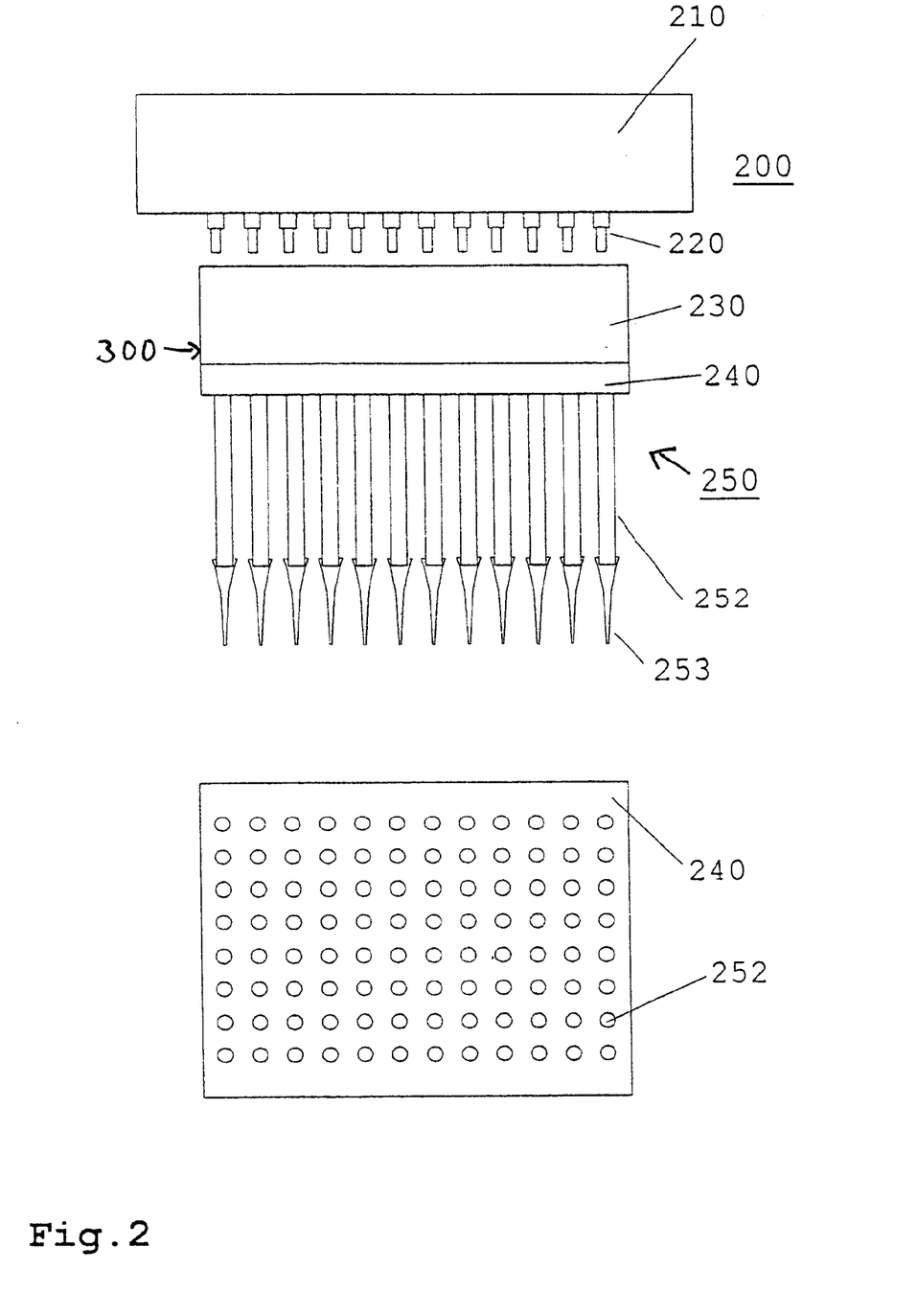
FIG. 2 is a diagrammatic view to illustrate how an actuating matrix interacts with a plurality of metering devices according to a first embodiment of the invention.

FIG. 2 shows details of the metering head according to the invention to illustrate how the actuating elements cooperate with the metering devices. The metering station 200 consists of an actuating matrix 210, a mounting block 300 and the metering devices 250 (micropipettes here, for example). The actuating matrix 210 consists of the pneumatic cylinders, which each have an actuating needle 220. As described above, the pneumatic cylinders can be activated by operating the respective solenoid valve, so that the actuating needle 220 is pressed to the end of an activating pin of an accompanying metering device in the mounting block 300. For reasons of clarity in FIG. 2 (left) the actuating needles 220 are spaced from the mounting block 300. However, in practice, the actuating needles 220 touch the ends of the activating pins (e.g., pipette pistons) of the metering devices in the basic position.

The mounting block 300 consists of a guide block 230 and the carrier plate 240, from which the micropipettes 252 extend downwards with the pipette tips 253 pointing to a carrier substrate.

The right side of FIG. 2 shows the matrix arrangement of micropipettes 252 with a diagrammatic view of the carrier plate 240 from below. The micropipettes 252 arranged in columns and rows project out of the carrier plate 240, with their configuration here corresponding just to the position of 96 microtiter volumes or containers of a microtiter plate.

Figure 3:
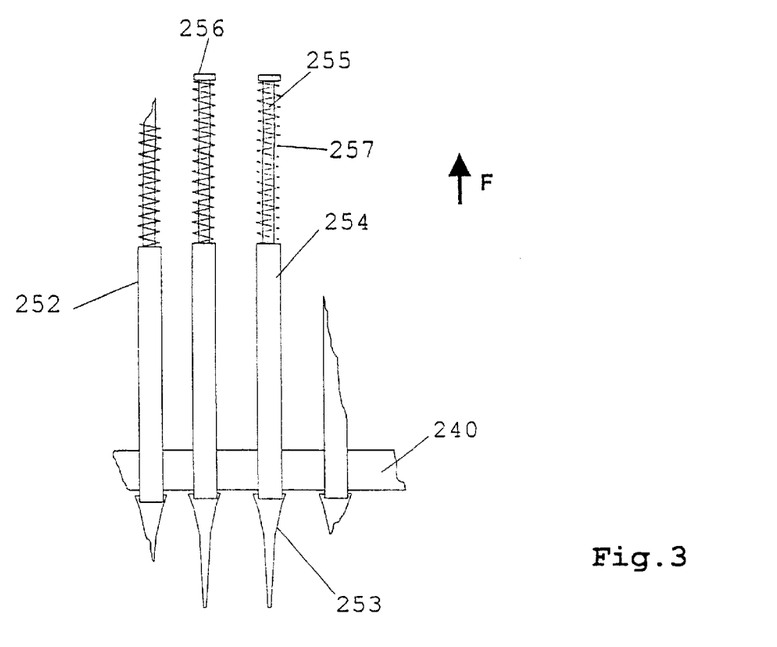
FIG. 3 is a sectional view of the attachment of micropipettes according to the invention.

In FIG. 3 partial views of details relating to how the micropipettes are attached in the mounting block 300 are shown. Each micropipette 252 consists of a cylinder 254 with the pipette tip 253 at one end and the activating pin 255 (end of the pipette piston) at the other end. Inside of the cylinder 254, the pipette piston is retracted by a piston spring between the upper cylinder end and lower piston end. A pin spring 257 slightly biased in the basic position is provided between the end support 256 of the pipette piston 255 and the cylinder 254. In the embodiment of the invention shown on FIG. 3, the cylinders 254 are securely attached to the carrier plate 240. In the basic position, the pipette piston 255 is completely retracted by spring force (arrow F), thereby providing for a large pipetting volume in the cylinder. When the accompanying actuating element is actuated (see FIG. 2), a pneumatic cylinder of the actuating matrix 210 presses an actuating needle 220 to the end support 256. The pneumatic cylinder works against the spring force of the pin spring 257 and the internal piston spring, and pushes the pipette piston 255 toward the pipette tip. When removing the working pressure from the pneumatic cylinder, the pipette piston 255 returns again under the action of to the pin and piston springs 257. When the metering head is used as intended, these movements of the pipetting piston 255 between the basic state and the tensioned state are used for taking a sample from a sample container or effecting the corresponding sample release.

In the above implementation of the invention with picking needles, the latter are guided in external cylinders, similarly to the pipette pistons, and project from the ends of the guide cylinder for the process of immersion into a sample.

The micropipettes according to FIG. 3 can be adjusted for uptaking or releasing predetermined fluid volumes, e.g., ranging from about 1 $\mu$l to about 200 $\mu$l. Given a sufficiently constant working pressure, the pipetting volume in the cylinder 254 can be set using the variable switching time of the pneumatic cylinders.

When using a metering head with a metering station according to FIG. 3, all pipette tips are immersed in the sample container during the pipetting process. However, only specific pipette tips are filled with sample material based on the predetermined addressing of the actuating matrix. The metering head is then moved to another substrate carrier or a different substrate carrier position for sample release or additional manipulation.

The embodiment of the invention incorporating selectively activatable micropipettes advantageously enables the following applications.

When establishing a partial collection from a collection of organic or inorganic solutions (e.g., a natural or man-made products library), individual samples (e.g., numbering up to 96) can be taken from the mother plates, and then transferred into a sister plate. This is followed by a washing stage with vacuum treatment (vacuum suction) to remove residual substance at the pipette tip and avoid contamination during the ensuing pipetting steps.

When collecting a specific saline solution of varying concentration in a microtiter plate, e.g., as is of interest in a protein crystallization experiment, predetermined concentration gradients can be generated by the individual pipetting processes according to the invention.

If specific individual clones have been found to be defective (e.g., contamination, no vector, no insert, etc.) in a gene library (genome or cDNA), the metering head according to the invention can be used to effectively remove the defective individual clones from the microtiter plates. After a first step to remove the individual clone, a purification step takes place on the corresponding microtiter volume, in which the microtiter volume is rinsed with a disinfectant solution, for example.

The possible applications mentioned here constitute a major advance relative to the previously used picking needle robotic heads with sequentially operated picking needles, which could only handle the tasks specified here on a limited basis, if at all.

Figure 4:
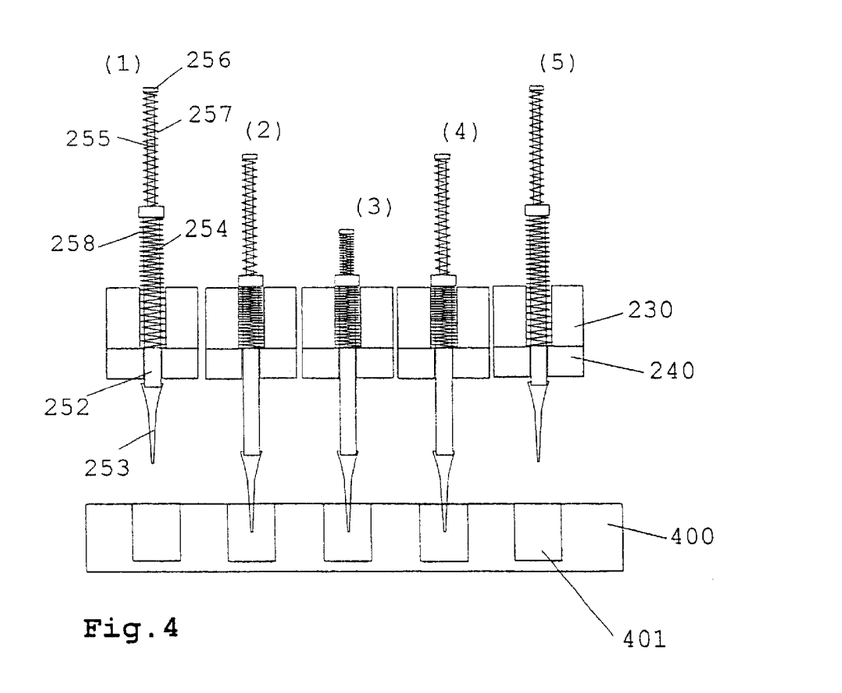
FIG. 4 is an illustration of the two-step actuation of micropipettes according to another embodiment of the invention.

FIG. 4 shows an alternative structural design in which activating a pneumatic cylinder of the actuating matrix 210 (see FIG. 2) moves not just the pipette pistons of the accompanying micropipette, but also the pipette cylinder. In this embodiment (FIG. 4), the micropipette 252 again consists of a cylinder 254 with the pipette tip 253 and pipette piston 255, whose end support 256 interacts with the actuating needle (not shown) of the actuating matrix. The carrier plate 240 and the guide block 230 form a mount for the micropipettes 252, in which the latter can be moved between a retracted basic state (upper stop) and an advanced pipetting state (lower stop) in a direction perpendicular to the plane of the carrier plate 240. To this end, each micropipette 252 is provided with a cylinder spring 258 between the upper cylinder end and the carrier plate 240 in addition to the pin spring 257, wherein the springs interact as follows with the pin spring 257 to realize the sequences of movement between the basic and pipetting state.

According to the invention, the cylinder spring 258 that biases the end of the cylinder 254 against the carrier block 240 has a lower spring rate than the pin spring 255, which biased the end of the pipette piston 256 against the end of cylinder 254. The ratio between the spring rates is selected such that, when an actuating force acts on the end support 256, the cylinder springs 258 are first compressed via the harder pin spring 257, and only then the pin spring 257 will be compressed. In practice, both processes can overlap, but the movement of the micropipette from the basic to pipetting state is to take place significantly faster than the movement of the pipette piston 255 from the basic state to the biased state. In a preferred embodiment of the invention, the spring rate of the cylinder spring is about a factor of 10 smaller than the spring rate of the pin spring. The individual sequences of movement which take place are illustrated in FIG. 4.

State (1) shows the micropipette in the basic condition, i.e., both the pipette piston 255 and cylinder 254 are in the retracted, upper position. State (2) shows the movement of the cylinder 254 from the basic to the pipetting position, in which the selected pipette is lowered into the microtiter volume 401 of a microtiter plate 400, for example. Positions (3) and (4) correspond to the actual pipetting process, in which the pipetting pistons 255 are moved to the biased position (small pipette volume) (3) and then retracted for taking up a sample fluid (4). The cylinder springs 258 then initiate a backward movement to the basic state of the pipette (5).

The advantage to the configuration shown on FIG. 4 is that those pipettes that are not required in a programmed pipetting process do not dip into the microtiter volumes, thereby preventing contamination. This is particularly advantageous when pipetting living organisms or cells or other biologically highly active substances (e.g., DNA) in solutions. In one pipetting process according to the invention, the metering head is first moved over the carrier substrate (e.g., microtiter plate) and advanced into the volumes of the carrier substrate based on the addressing of the actuating matrix (see FIG. 2) between 1 and 96 pipettes. The samples are then taken or released with the selected pipettes. After the respectively selected pneumatic cylinder is released, the pipette pistons are first moved upward (drawing in of sample fluid), after which the pipette cylinders themselves are retracted.

One special advantage to the invention is that the process described here be freely programmed and made to run in parallel.

Figure 5:
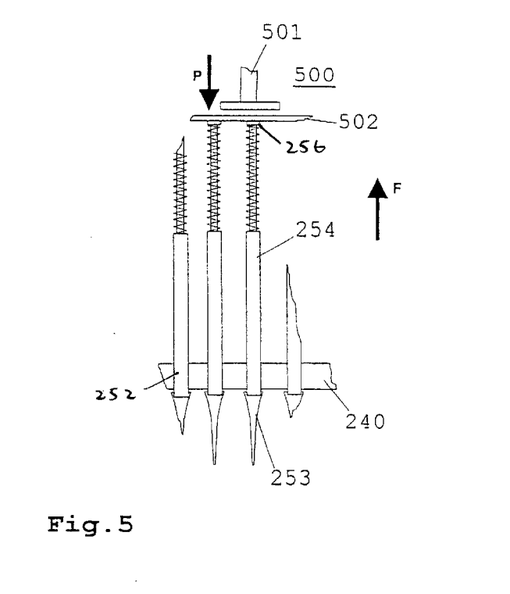
FIG. 5 is a diagrammatic sectional view of another embodiment of the invention.
Figure 6:
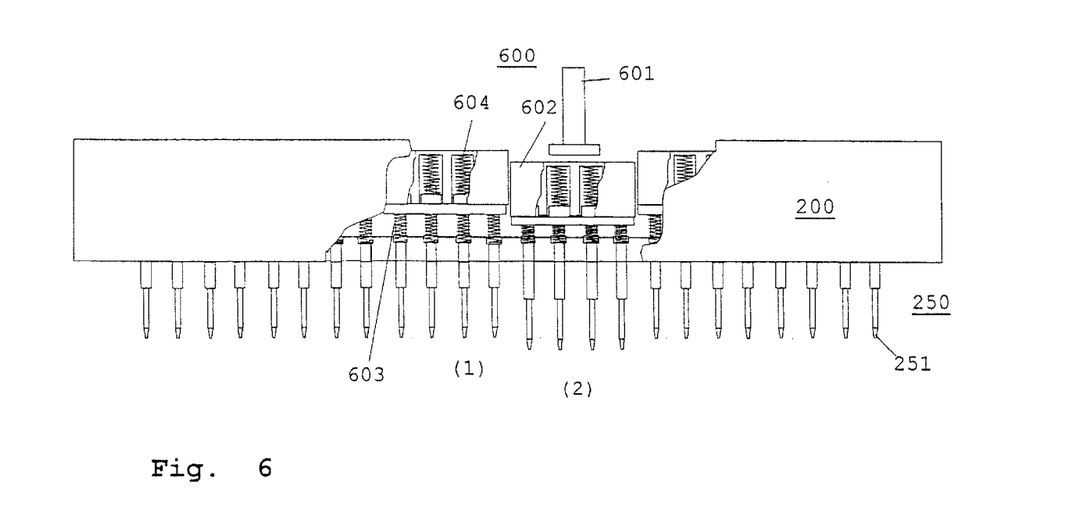
FIG. 6 is a diagrammatic sectional view to illustrate the block formation according to the invention.

Another embodiment of the invention is shown in sections in FIGS. 5 and 6. The configuration and attachment of the micropipettes 252 are here substantially the same as the structural design shown on FIG. 3, wherein a coupling device 500 or a block frame 600 (see FIG. 6) is additionally provided for the simultaneous or block-wise activation of numerous micropipettes. The coupling device 500 consists of a cylinder device 501 and a plate element 502 (so-called "backplate"). The plate element 502 is provided between the end supports 256 of the pipettes 252 and the cylinder device 501. In a preferred embodiment, the cylinder device 501 is formed by some or all of the actuating needles 220 (see FIG. 2). The purpose of the cylinder device 501 is to exert a uniform activating force (arrow P) on all pipettes encompassed by the plate element 502. The plate element 502 is inserted between the ends of the pipettes and the actuating matrix 210 as a thin plastic or sheet component with the carrier plate 240 removed (see FIG. 2).

In this embodiment, the pipetting process takes place in such a way that all pipette pistons are first moved inside of the pipette cylinder before the pipette tips are immersed in the fluid-filled sample containers. The lift determines the quantity of liquid to be absorbed as a result. In addition, the lift can be set via mechanical stops. Lowering the metering head submerges all pipette tips into the sample container. After the force P exerted by the cylinder device 501 has been released, the pipette pistons are simultaneously moved upward by the pin springs, during which the same fluid volume, e.g., ranging from about 1 to about 200 μl, is taken up in all pipettes. The samples are released by ejecting the fluid in the corresponding sequence in reverse.

The advantage to the configuration described on FIG. 5 is that sample uptake or release is uniform and balanced for all pipettes comprised by the plate element 502. If desired the plate element 502 inserted into the metering station does not combine all, but only a portion of the pipettes corresponding to a predetermined grid.

The configuration according to FIG. 5 is advantageous in particular for the following applications of a picking/spotting system. When used in high-throughput screening in systems for active agent localization, samples are taken in parallel with volumes identical in all cases from microtiter plates with 96 or 384 individual samples. Libraries of natural or man-made substances can again serve as the samples, but so, too, can other collections of substances, substance mixtures or biological systems like microorganisms, vegetable, animal or human cells. The samples are then transferred to test containers inside of the system, where the predetermined analysis for biological or physiological efficacy or properties takes place. In a centrifugation stage outside the system, residues from the individual expression clones can be imbibed from microtiter plates in protein expression libraries and transferred to test vessels (e.g., membranes or other microtiter plates).

In addition, the parallel removal of defined fluid volumes for purposes of distribution to new sample containers or mixing with other substances is facilitated. For example, this is of interest for testing of substances (antigens, antibodies, etc.) in ELISA tests, initiating enzymatic reactions (restriction digestion, PCR, etc.) or testing enzyme specificities.

Finally, parallel pipetting of substances in solutions according to the invention is used to synthesize new substances (combinatory chemistry). Synthesis can here take place on fixed substrate carriers (e.g., plastic surfaces in microtiter plates or membranes) or in solutions. Examples include the synthesis of peptides or oligonucleotides on membranes.

Another variation of the embodiment of the invention shown in FIG. 5 is shown to illustrate the block-by-block activation of metering devices on FIG. 6. FIG. 6 shows a sectional view of a metering station 200 with a partially open depiction of the casing wall. Based on the embodiments described above, the metering station encompasses a matrix of metering devices 250 in the form of picking needles 251. The picking needles 251 form a 16×24 grid corresponding to a 384 microtiter plate. The needles are combined into needle blocks with a grid of 4×4 needles. Block formation is provided by a block device 600 that encompasses a block frame 602 with accompanying activating element 601 for each block. The block frames 602 have the same function as the aforementioned plate element 502, and are intended to impart the force exerted by the activating element 601 to all needles belonging to a block simultaneously. The block frames each encompass a connecting rack, to which the metering devices belonging to a block are attached. The picking needles are each mounted with two springs, namely with a restoring spring 603 for the block frames 602 (or connecting rack) and a compensating spring 604 for the picking needles. The compensating springs 604 offset the minimal height differences between the picking needles as they are placed on a substrate. To this end, the metering devices are mounted on the block frame over the compensating springs 604 in such a way that they can shift in an axial direction. The needle blocks can be transferred individually from a basic position (1) into a lowered position (2) by activating the element 601. The activating element 601 can be a pneumatic cylinder or an electric lifting magnet. The mentioned 384 grid has a total of 24 needle blocks. This block formation can be adapted to the shape of the respective target as a function of application, wherein the 4×4 sub-grid is suitable in particular for the ensuing metering or sample manipulation processes. The activating element 601 can also encompass a group of actuating needles of the needle matrix described above corresponding to the group of activated metering devices. Hence, the block arrangement 200 can be provided as an exchangeable module of a metering station, similarly to the replaceable carrier plate described above.

A metering station according to FIG. 6 can, for example, transfer any substance present in dissolved form in a microtiter plate to a carrier matrix with a specific format. For example, the nucleic acids synthesized in a polymerase chain reaction (PCR) are removed from the 384 recesses of the microtiter plate of the metering head and transferred to a flat target (e.g., glass carrier) in as tight an arrangement as possible. Typical spot distances and spot densities are 15×15 spots at a 500 µm distance (225 spots/cm$^2$, in particular for bacterial cultures) or 50×50 spots at a 50 µm distance (2500 spots/cm$^2$, in particular for PCR products). The expression of a gene represented by a PCR product can be detected and quantified in a specific tissue via hybridization with suitable specific probe substances that are not marked by radioactive procedures, e.g., fluorescent dyes. Block formation according to the invention enables a highly tight arrangement of the PCR products on the glass carrier by unloading the needle blocks activated in parallel on the microtiter plate at the glass carrier block for block and in sequence, wherein the metering head is traversed a specific distance (corresponding to the desired spot distance) between two deposits on the glass carrier. This process cannot be realized with conventional, individually activated 4×4 needle matrixes, which additionally require a separate washing step in each work stage.

Figure 7A:
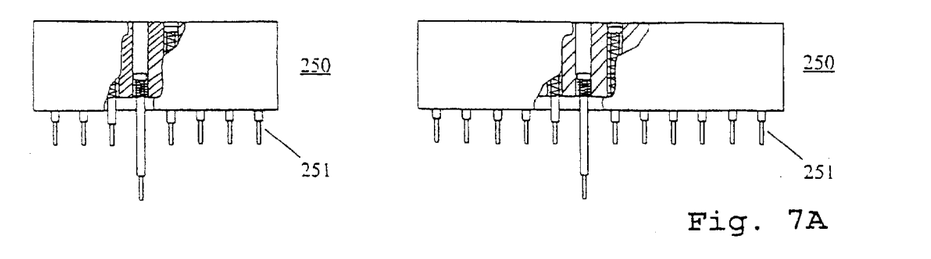
FIGS. 7A–7D are other illustrations of the metering stations of metering heads according to the invention.
Figure 7B:
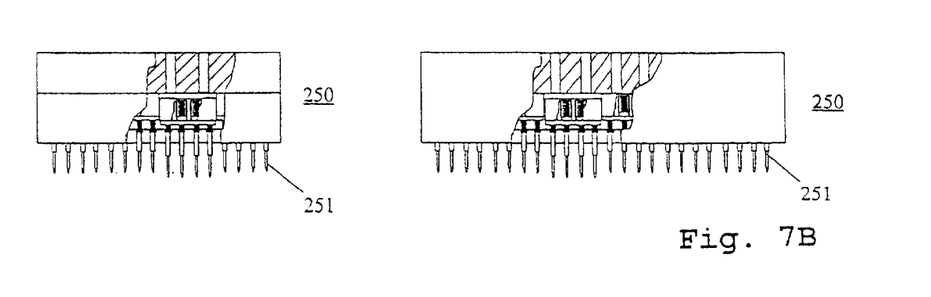
Figure 7C:
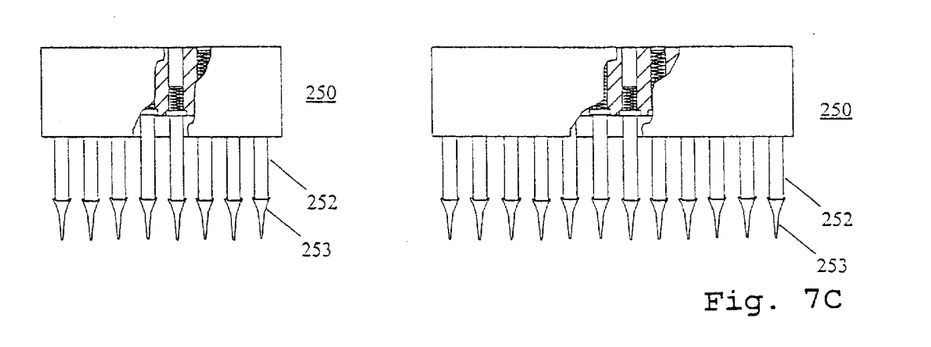
Figure 7D:
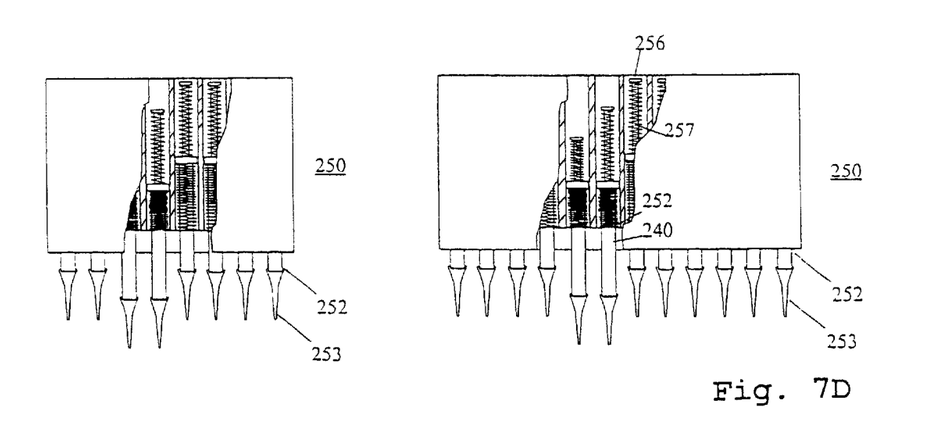

FIGS. 7A to 7D illustrate additional metering stations with partially open depiction of the casing wall for various grid formats of the metering devices. The narrow side view of the metering stations is shown on the left of the figure, the broad side view on the right. According to FIG. 7A, the picking needles 251 form an 8×12 grid corresponding to a 96 microtiter plate. Each picking needle 251 can be actuated with a separate pneumatic cylinder (see above). As in FIG. 6, FIG. 7B shows an arrangement with a 16×24 grid, wherein 24 blocks are formed, each with 4×4 picking needles. FIG. 7C shows one embodiment with 96 micropipettes 252, 253. This corresponds to a grid of 8×12 micropipettes. While the pipette arrangement on FIG. 7C is shown without an advanced micropipette, FIG. 7D depicts a case where the micropipette is advanced (see also FIG. 4).

The results of hybridization on the glass carriers are then evaluated in a computer-assisted image analysis. The metering head according to the invention makes it possible to arrange the PCR products with a density, accuracy and reproducibility required for image analysis. As a result, the sample throughput can be increased by a factor of about 10.

However, the use of the metering head according to FIG. 6 is not limited to bringing out nucleic acids on carrier substrates. With the continuing miniaturization of the test and detection procedure, another application of the microarrays according to the invention will be in the functional analysis of expressed proteins present in the microtiter format.

Therefore, the invention also relates to a procedure for generating sample micro-arrays, in which the substances or samples to be tested are transferred in dissolved form from an ordered matrix (e.g., microtiter plate) to a surface whose area is smaller than the dimensions of the original matrix configuration. Both the quantity of substances brought out and the volume of detection reagents can be greatly reduced by the extremely tight arrangement of the spots relative to conventional methods. The transfer procedure can be followed by a detection procedure, in which a measuring signal (e.g., fluorescence measurement) is detected in a locally limited manner.

The metering head described above can be modified as follows. In the operating position the metering can take place not just downwards to the bottom but, given the appropriate metering devices, also along the horizontal. Depending on the application, the two-phase activation of micropipettes according to FIG. 4 can be supplemented with additional phases of movement by providing additional recuperating springs, with respectively adjusted spring rates. The metering head according to the invention can advantageously be combined with the elements of a picking/spotting system.

What is claimed is:

1. A metering head that is freely movable using a device for traversing the metering head, the metering head comprising:

a plurality of metering devices, which, as individual metering devices or as metering device blocks, are provided with respective activating devices individually or in blocks, wherein the metering devices comprise picking needles or micropipettes arranged in accordance with orientation of sample volumes in a microtiter plate, the activating devices each being formed by a pneumatic cylinder having an actuating needle for activating the metering devices or metering device blocks, and a controller traversable with the metering devices provided with control outputs whose number at least equals the number of pneumatic cylinders and which are connected with an accompanying control output by a pressure line, such that the metering devices or metering device blocks can be independently activated during metering head operation.

2. The metering head according to claim 1, in which the metering devices are arranged in a matrix and the pneumatic cylinders form an actuating matrix cooperating with the metering devices arranged in said matrix.

3. The metering head according to claim 1, in which the metering devices or metering device blocks form a metering station which is a detachable part the metering head as a replaceable module.

4. The metering head according to claim 3, in which the metering station includes an actuating matrix and a mounting block, to which picking needles or micropipettes are secured such that their upper end supports are oriented essentially in one plane, and ends of the actuating needles contact the actuating matrix.

5. The metering head according to claim 4, in which the metering devices are micropipettes secured to a carrier plate of the mounting block, each micropipette having a pipette piston, which is biased by a piston spring against the cylinder of the micropipette.

6. The metering head according to claim 5, in which the micropipettes can be axially moved relative to the carrier plate, and wherein the cylinder of the micropipette is biased by a cylinder spring against the carrier plate.

7. The metering head according to claim 6, in which a spring rate of the cylinder spring is less than a spring rate of the piston spring.

8. The metering head according to claim 7, in which, upon activation of an accompanying actuating needle, each micropipette can first be moved from a basic position into a pipetting position by compressing a corresponding cylinder spring, and then be activated to release pipetting output by compressing the corresponding piston spring.

9. The metering head according to claim 1, wherein 96 or 384 metering devices are provided.

10. The metering head according to claim 1 in which a plate element is provided between an actuating matrix and the metering devices, which connects end supports of blockwise arranged or all metering devices with each other.

11. The metering head according to claim 1 in which plate elements or block frames are provided, with which the metering devices are connected in blocks.

12. The metering head according to claim 11, in which an actuating matrix comprises the actuating needles whose number corresponds to a number of plate elements or block frames.

13. The metering head according to claim 1, further comprising a lid station and/or a gripper station.

14. The metering head according to claim 1, wherein the metering devices are micropipettes having a cylinder, a pipette tip, a pipette piston, a piston spring that biases the pipette piston against the cylinder, and a cylinder spring that biases the cylinder against a carrier, which forms a guide for the axial movement of the micropipette against tension of the cylinder spring.

15. The metering head according to claim 14, in which the cylinder spring has a lower spring rate than the piston spring.

16. A picking/spotting system equipped with a metering head according to claim 1.

17. A method of taking or releasing a plurality of fluid samples using a metering head according to claim 1, comprising individually or simultaneously activating metering devices to take samples from a carrier substrate or place them on the carrier substrate.

18. The method according to claim 17, comprising manipulating samples in substance libraries for molecular genetic, biochemical or medical purposes.

19. The method according to claim 17, comprising substantially simultaneously taking samples from a carrier substrate with all metering devices and sequentially placing said samples on a target substrate block-wise, and wherein the metering head traverses over a predetermined path after each sample deposition with one respective block of the metering devices.

* * * * *